United States Patent [19]

Bowen et al.

[11] Patent Number: 4,853,517
[45] Date of Patent: Aug. 1, 1989

[54] VAPORIZING UNIT

[75] Inventors: John G. Bowen, 2815 Industrial Rd., Santa Fe, N. Mex. 87501; John M. Groome, Hemel Hempstead, England

[73] Assignee: John G. Bowen, Santa Fe, N. Mex.

[21] Appl. No.: 174,460

[22] Filed: Mar. 28, 1988

[51] Int. Cl.⁴ ............................................. H05B 3/14
[52] U.S. Cl. ................................. 219/271; 219/274; 219/275; 219/504
[58] Field of Search ............... 219/271, 272, 273, 274, 219/275, 276, 432, 439, 430, 441, 504, 505, 433

[56] References Cited

U.S. PATENT DOCUMENTS

| | | | |
|---|---|---|---|
| 3,872,280 | 3/1975 | Van Dalen | 219/271 |
| 4,163,038 | 7/1979 | Nishimura | 219/275 |
| 4,177,375 | 12/1979 | Meixner | 219/439 |
| 4,223,208 | 9/1980 | Kleinschmidt | 219/439 |
| 4,354,822 | 10/1982 | Madsen | 219/271 |
| 4,700,050 | 10/1987 | Hennuy | 219/275 |
| 4,703,155 | 10/1987 | Suhajda | 219/271 |
| 4,725,712 | 2/1988 | Schroeder | 219/275 |
| 4,731,522 | 3/1988 | Manchester | 219/272 |

*Primary Examiner*—Teresa J. Walberg
*Attorney, Agent, or Firm*—Keith D. Beecher

[57] ABSTRACT

An electrically energized vaporizing unit for medications, room deodorizers, room scenting compounds, room insecticides, and the like, which is simple and inexpensive in its construction and which is compact in size. The vaporizing unit includes a housing having a central slot for holding a compressed paper fiber pad which is impregnated with the substance to be vaporized. The pad is heated by a pair of electrical heating elements which are located in the housing and positioned on opposite sides of the slot for maximum vaporizing efficiency of the pad. The housing may also contain paraffin wax. The melting point of the wax is selected to correspond to the vaporizing temperature of the particular substance in the pad. The vaporizing unit is provided with an electric plug which may be directly plugged into an electric receptacle to energize the PTC heating elements, and it does not require a switch or protective thermostat.

11 Claims, 3 Drawing Sheets

VAPORIZING UNIT

BACKGROUND OF THE INVENTION

The vaporizing unit of the present invention is similar in some structural respects to the vaporizing unit described in Copending Application Ser. No. 5,146 which was filed Jan. 20, 1987 in the name of the present inventor.

The prior art vaporizers, for the most part, use steam to vaporize a medication or other substance, so that the medication may be raised to a constant vaporizing temperature, the boiling point of water and held at that temperature only while water is available to be boiled in the reservoir of the vaporizer. However, this means that the medicinal effects, for example, of the vaporized substance are diluted by the steam. The presence of steam may have disadvantages or advantages to achieving the desired medicinal effects. The vaporizer of the present invention, like the vaporizer of the Copending Application, provides a dry vaporizing action by which the medication, or other substance to be vaporized, is vaporized directly at the most appropriate vaporizing temperature for a period of time that is only dependent on the electrical supply, and operates in an undiluted manner.

The vaporizing unit of the invention, in one of its embodiments, like the unit described in the Copending Application, uses paraffin wax, or the like, to transmit the heat from the heating elements to a compressed paper fiber pad impregnated with the substance to be vaporized so that a predetermined temperature may be established for the pad which remains constant over prolonged periods of time.

When the substance to be vaporized from the pad is a liquid, such as a medication, insecticide or perfume, it is absorbed into the pad, which is usually a compressed paper fiber pad. Examples of such commercially available pads for pesticide applications include "Pif-Paf" marketed by The Wellcome Foundation Ltd., Berkhamsted, Hertfordshire, England; "Revenge" marketed by Aeroxon Products, Inc., New Rochelle, N.Y., U.S.A.; and "Vape Mat F" marketed by Fumakilla Ltd., Tokyo, Japan.

These pads are usually manufactured from a large sheet of compressed paper fiber with a final thickness of about $\frac{1}{8}$th of an inch. Prior to compression the paper fiber pulp may have a thickness of as much as $\frac{3}{8}$ths of an inch. The force involved in the compression tends to align the long dimension of the paper fibers at right angles to the applied force, that is to say along the length of the pad with the small cross section of the fibers towards the edges of the pad. These large pads are then cut to the required dimensions for use in the appropriate vaporizer and are impregnated with the liquids to be vaporized and other components of the product formulation.

Vaporizers of the type disclosed in the Copending Application Ser. No. 005,146 apply heat to only one of the large faces of the pad. Such vaporizers are currently the only ones in commercial use.

Experimentation with that type of vaporizer showed that as one of the faces of the pad was heated, liquids impregnated in the pad tended to move to the edges of the pad rather than to the exposed face which was not heated. The impregnated liquid was found to move along the long axis of the compressed fibers by capillary action which was initiated by thermal diffusion. Only small amounts of impregnated liquid were found to move to the unheated face of the pad since the alignment of the fibers prevented capillary action and therefore movement was solely by thermal diffusion. This resulted in an inactive "dead space" in the pad under the unheated face and impregnated liquid trapped in this area did not contribute significantly to vaporization. The practical result of these findings was that the unheated face of the pad was significantly colder than the heated face and that vaporization of the impregnated liquid occurred mainly at the edges of the pad, with very little release of vapor from the unheated face.

The vaporizing unit of this invention greatly increases the vaporizing efficiency of the pad by heating it from both faces. Such a vaporizer has the distinct advantage over the vaporizer of the Copending Application in that when operating at a given temperature more heat energy is introduced into the pad, and the pad does not have a "cold" face. Heating both faces of the pad increases the rate of thermal diffusion of the impregnated liquid within the pad and its movement to the edges of the pad by capillary action. Therefore more impregnated liquid is available at the edge of the pad for release and vaporization.

Vaporizing units of the type disclosed in this invention have several other advantages over those currently available that only heat one face of the pad. They have a more even vapor release pattern, with the initial release of the active components occurring more rapidly and continuing for longer periods at a more steady level. This occurs because more of the active component can move to the edges of the pad when it is heated from both sides as there is no impregnated liquid trapped in an inactive "dead space" in the pad under an unheated face.

The double sided vaporizing unit of the invention is safer to use than the unit of the Copending Application since it can operate at a lower temperature, providing that the temperature is above vaporization temperature of the active component to be released from the pad, since it applies more heat energy more evenly to the pad. Operating the vaporizing unit at a lower temperature also has the advantage of reducing any thermal degradation of the impregnated liquids that could reduce their activity and increase any toxicity caused by the products of such degradation.

SUMMARY OF THE INVENTION

The invention provides an electrically energized vaporizing unit including an embodiment in which the substance to be vaporized is contained in a compressed paper fiber pad which is heated from both sides by positive thermal coefficient (PTC) electrical heating elements in conjunction with paraffin wax. The melting point of the wax is selected to match the vaporizing temperature of the substance in the pad. This enables the temperature of the substance to be raised to its vaporizing level and held at that level over long periods of time. The unit may be used for medicinal purposes, or for room scenting, deodorizing, or the like. In addition, the unit may be used for vaporizing an insecticide into the surrounding environment.

The embodiment of the invention to be described includes a housing configured to provide a central slot for receiving the pad. The housing contains a pair of PTC heating elements positioned on opposite sides of the slot, and the housing also contains a quantity of paraffin wax. This construction assures that heat from the heating elements is transmitted to both sides of the pad in a manner to maximize the vaporization of the substance in the pad.

BRIEF DESCRIPTION OF THE DRAWINGS

FIG. 3 is a perspective view, like the view of FIG. 2, but with one side of the slot in the housing broken away to clarify the construction of the unit;

DETAILED DESCRIPTION OF THE ILLUSTRATED EMBODIMENT

Figure 1:
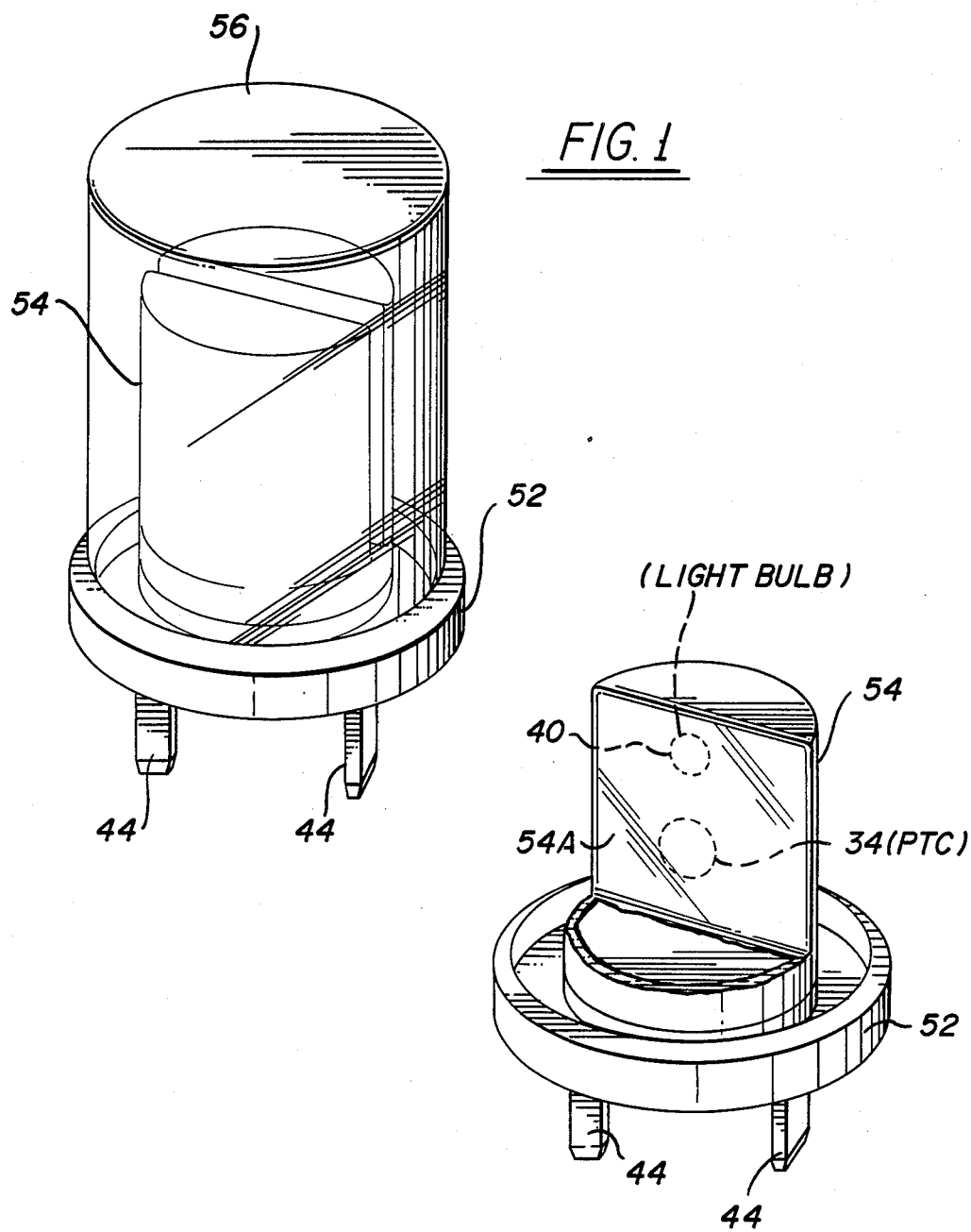
FIG. 1 is a perspective view of one embodiment of the invention with its outer cover in place.

The vaporizing unit illustrated in FIGS. 1-3 and FIG. 5 includes a base 52. Two pins or blades 44 are mounted on the base, and extend downwardly from the base to permit the unit to be plugged directly into an electric receptacle.

A housing 54, preferably formed of glass, is mounted on base 52. A pair of PTC heating elements 32 and 34, and one or more of light bulbs 40, are contained and sealed in the housing 54. The heating elements are embedded in paraffin wax which is also contained in the housing.

Figure 2:
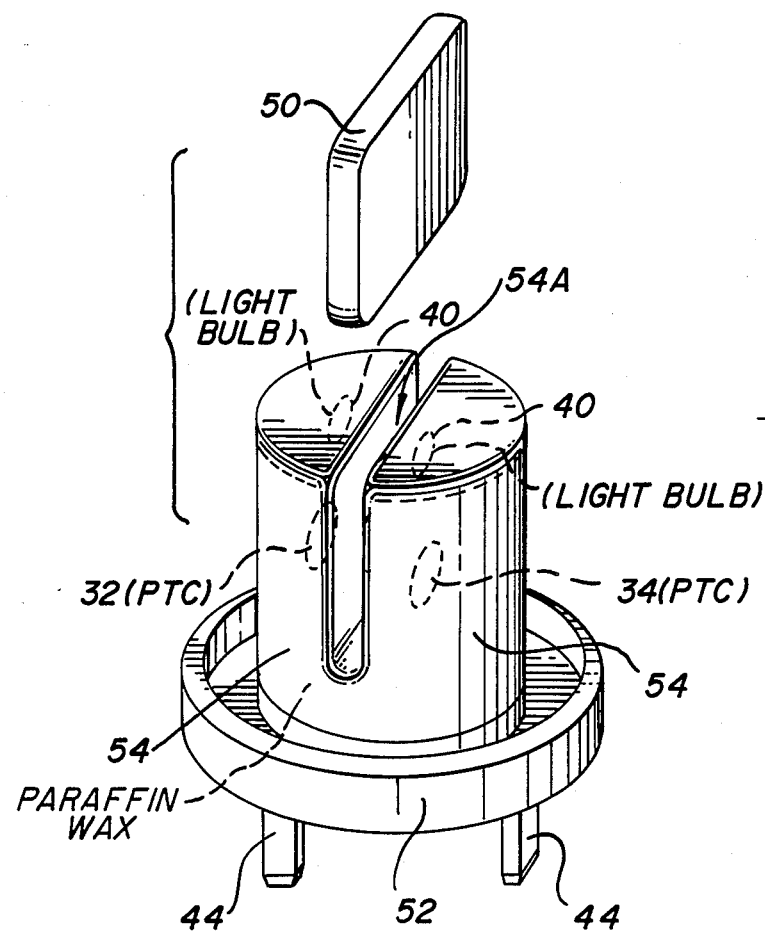
FIG. 2 is a perspective view of the embodiment of FIG. 1, with the outer cover removed, and illustrating a central slot in the housing of the unit which is intended to receive a solid tablet saturated with the substance to be vaporized.

The housing 54 has a generally cylindrical shape, as shown in FIGS. 2 and 3, and is configured to form a central slot 54A which is intended to receive a compressed paper fiber pad 50. The heating elements 32 and 34 are positioned on opposite sides of the slot, and the construction is such that the majority of the heat from the interior of housing 54 is directed to the pad 50. A small projection may be formed on one edge of the slot in the event the housing is supported in a horizontal position by the electrical receptacle.

The compressed paper pad 50 is impregnated with the substance to be vaporized. The pad 50 may be disposable and of any of the types referred to above, or it may be rechargeable. The PTC heating elements 32 and 34 are composed of a semiconductor ceramic, such as appropriately doped barium titanate. As is known to the art, this material has a positive thermal coefficient, and it has a property that at a certain temperature, known as the Curie point, its internal resistance suddenly increases if temperatures are raised above that point.

Accordingly, the PTC heating element is attractive because of its automatic temperature control characteristic. The PTC heating element is independent of voltage, and can be used in conjunction with alternating current or direct current. Regardless of voltage, the element will increase in temperature until the Curie point is reached, and at that point it will effectively cut off, serving inherently as an automatic temperature controller. Moreover, the PTC heating element does not require a protective relay in its circuit, because it is incapable of burning out. These features enable the unit of the invention to be used worldwide, in conjunction with alternating current or direct current sources of various voltages.

The Curie point of the PTC heating element can be set to any desired temperature level by the selection of the doping of the ceramic material. In the case of the vaporizing unit of the invention, this level is set to correspond with the vaporizing temperature of the substance contained in the solid tablet 50.

It is known that the Curie point cannot be set with any degree of accuracy, and variations up to ±40% have been experienced from one PTC heating element to another. However, in the vaporizing unit of the present invention, the PTC heating elements 32 and 34 are embedded in paraffin wax, and the wax is used to carry the heat from the heating elements to the slot.

The paraffin wax in the housing is selected to have a melting point which corresponds with a high degree of accuracy with the vaporizing temperature of the particular substance to be vaporized from the solid tablet. The Curie point of the PTC heating elements is then set to occur above the melting point of the wax, even with its widest variation. During normal operation the wax is never completely melted, and its latent heat establishes a precise vaporizing temperature for the vaporizing unit.

Figure 4:
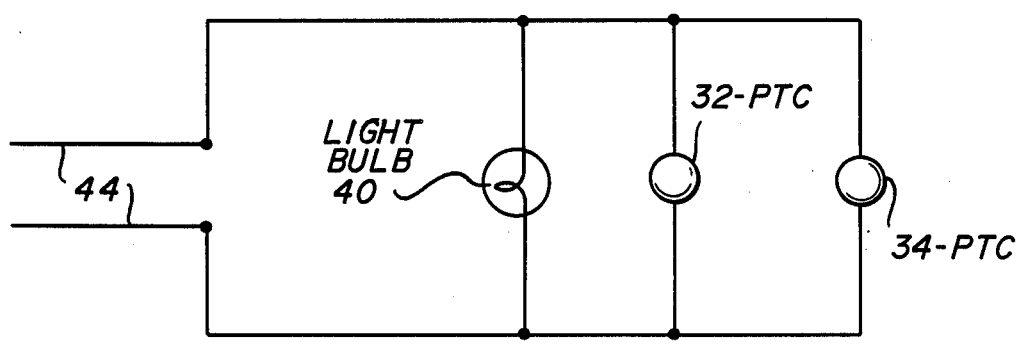
FIG. 4 is a simplified circuit diagram showing the manner in which the PTC heating elements in the unit are connected and energized.
Figure 5:
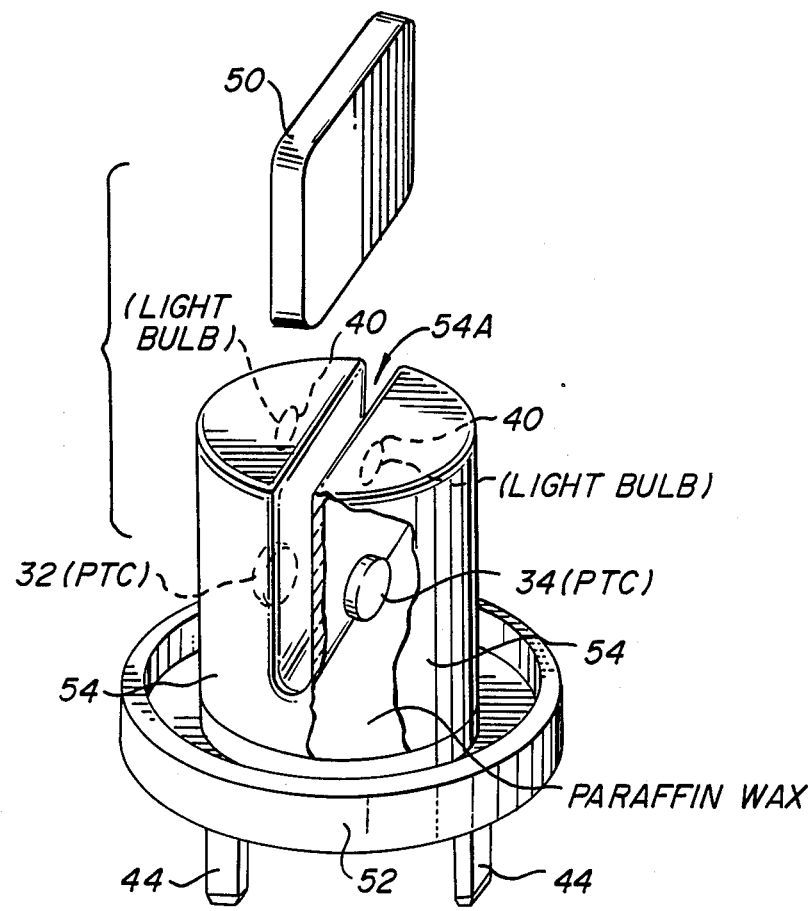
FIG. 5 is a view like FIG. 5, but partly in section.

As mentioned above, there is no need for a cut-off relay in the circuit of FIG. 4 because, if for any reason the PTC heating elements are heated above the normal operating temperature of the vaporizing unit (a condition which could occur should the heating elements come out of contact with the wax), the increased temperature never exceeds the Curie point. Thus, the heating elements 32 and 34 are capable of achieving a precise vaporizing temperature insofar as the slot 54A is concerned.

During the entire operation of the unit, the pad 50 is held at the vaporizing point of the substance with which it is impregnated due to the latent heat of the wax contained in the housing, the wax being selected to have a latent heat corresponding to the desired vaporizing temperature. The light bulbs 40 glow to show that the nit is energized, and to show that the wax within the housing is in a molten state.

The unit continues to vaporize the substance in pad 50 over a substantial time period, and the vapor from the substance is discharged from the unit into the surrounding environment without being diluted by steam or other substance. if for any reason the temperature of heating elements 32 or 34 should rise above the vaporizing temperature, then, due to the inherent characteristics of the PTC units, they will cut off so as to form their own protective system.

An outer housing 56 may be provided for protective purposes to form a cover. Such a cover is required if the temperature reached by the housing 54 during operation would cause injury to the user. Appropriate apertures (not shown) are provided in the cover to permit the correct placement of the solid tablet, the removal of a used tablet, the inflow of air and the escape of vapor from the solid tablet.

The PTC heating elements 32 and 34 and light bulb 40 are connected across the pins 44, as shown in the electric circuit of FIG. 4. As mentioned above, there is no need for a cut-off relay in the circuit of FIG. 4 because, if for any reason the PTC heating elements are heated above the normal operating temperature of the vaporizing unit (a condition which could occur should the heating elements come out of contact with the wax), the increased temperature never exceeds the Curie point. Thus, the heating elements 32 and 34 are capable of achieving a precise vaporizing temperature insofar as the slot 54A is concerned.

The invention provides, therefore, a safe, simple, inexpensive and compact vaporizing unit which may conveniently be directly plugged into a wall electrical receptacle when in use. The vaporizing unit applies heat to both faces of the pad inserted into the slot in the housing of the unit. This provides for optimum efficiency in the vaporization of the substance in the pad as explained above. The unit has the feature in that the vaporizing action is created by dry heat, and without any necessity to generate diluting steam, or the like.

It will be understood, of course, that while a particular embodiment of the invention has been shown and described, modifications may be made. It is intended in the claims to cover all modifications which come within the true spirit and scope of the invention.

We claim:

1. An electrically energized vaporizing unit for directly vaporizing a substance from a pad impregnated with the substance, said unit comprising: a housing having a slot therein; a pad impregnated with a substance to be vaporized positioned in said slot; and electrically energized heating means mounted in the housing on both sides of the slot; electrical circuitry mounted in the housing for connecting the heating means to a source of electric energy.

2. The electrically energized vaporizing unit defined in claim 1, in which said heating means comprises a pair of PTC heating elements respectively mounted in said housing on opposite sides of said slot.

3. The electrically energized vaporizing unit defined in claim 2, and which includes a material contained in the housing for conducting heat from the heating means to the slot and which becomes at least partially molten after a particular time interval following energizing of the heating means, said material having a melting point corresponding to the vaporizing temperature of the substance contained in the pad, and said PTC heating elements having a Curie point above the melting point of the material.

4. The electrically energized vaporizing unit defined in claim 3, in which said material is paraffin wax.

5. The electrically energized vaporizing unit defined in claim 3, and which includes a base, and a pair of electrically conductive elongated members mounted on said base and protruding therefrom to form an electric plug, said electric circuitry being connected to said elongated members.

6. The electrically energized vaporizing unit defined in claim 5, in which said housing is mounted on said base and has a generally cylindrical configuration.

7. The electrically energized vaporizing unit defined in claim 6, and which includes an outer housing which may be fixed or removably mounted on said base coaxial with said housing.

8. The electrically energized vaporizing unit defined in claim 1, and which includes a material contained in the housing for conducting heat from the heating means to the slot.

9. The electrically energized vaporizing unit defined in claim 1, and which includes a base, and a pair of electrically conductive elongated members mounted on said base and protruding therefrom to form an electric plug, said electric circuitry being connected to said elongated members.

10. The electrically energized vaporizing unit defined in claim 9, in which said housing is mounted on said base and has a generally cylindrical configuration.

11. The electrically energized vaporizing unit defined in claim 9, and which includes a cylindrical cover removably mounted on said base coaxial with said housing.

* * * * *